United States Patent [19]

Jousson et al.

[11] Patent Number: 5,365,627
[45] Date of Patent: Nov. 22, 1994

[54] STEM BRUSH WITH AUTOMATIC INSERTION SYSTEM

[75] Inventors: Jean-Pierre Jousson, Chene-Bourg; Michel Moret, Geneva, both of Switzerland

[73] Assignee: Les Produits Associes. LPA-Broxo S.A., Geneva, Switzerland

[21] Appl. No.: 95,964

[22] Filed: Jul. 22, 1993

[51] Int. Cl.⁵ ............... A61C 17/34; A46B 13/02
[52] U.S. Cl. ................... 15/22.1; 15/176.6; 403/14; 403/380
[58] Field of Search .............. 15/22.1, 22.2, 23, 24, 15/176.1, 176.6; D4/100, 101, 102, 113; 403/11, 13, 14, 354, 356, 376, 380

[56] References Cited

U.S. PATENT DOCUMENTS

| | | | |
|---|---|---|---|
| D. 297,784 | 9/1988 | Moret | D4/101 |
| 3,088,148 | 5/1963 | Moret | 15/22.1 |
| 3,187,360 | 6/1965 | Spohr | 15/22.1 |
| 3,369,265 | 2/1968 | Halberstadt et al. | 15/22.1 |
| 3,400,417 | 9/1968 | Moret | 15/22.1 |
| 3,927,435 | 12/1975 | Moret et al. | 15/22.1 |

FOREIGN PATENT DOCUMENTS

| | | | |
|---|---|---|---|
| 2527130 | 1/1976 | Germany | 15/176.1 |
| 3129435 | 2/1983 | Germany | 15/176.1 |

*Primary Examiner*—Edward L. Roberts
*Attorney, Agent, or Firm*—Kane, Dalsimer, Sullivan, Kurucz, Levy, Eisele & Richard

[57] ABSTRACT

An oral hygiene device has a handle and an automatic stem insertion system and comprises a pair of keys on the motor driven shaft. A bore receives the shaft, and slots receive the keys. A pair of sleeves each having a ramp for receiving and engaging the keys. When coupling the stem to the handle and with a camming action of the keys on the ramp, the ramps guide the keys into the slots. A radially extending flange is on the base of the shaft; and a pair of flexible arms having a recess receive the flange. Upon coupling the stem to the handle, the flange engages the arms and flex the arms outwardly and further movement of the stem onto the handle causes the flange to enter the recesses with a snap action; and upon withdrawal of the stem from the handle, the flange causes the arm to flex outwardly to release the flanges from the recesses.

19 Claims, 5 Drawing Sheets

STEM BRUSH WITH AUTOMATIC INSERTION SYSTEM

BACKGROUND OF THE INVENTION a. Field of Invention

The present invention relates to an oral hygiene device comprising a stem brush, on a holder of an electric toothbrush. More specifically, the invention relates to an automatic insertion system for assuring the proper orientation and mounting of the stem brush on the holder.

b. Description of the Prior Art

Automatic stem brush insertion systems for oral hygiene devices have been proposed. For example, French Patent No. 2,276,015 discloses a stem brush with an automatic insertion system wherein the brush stem is snapped on a cylindrical shaft having a transverse pin. A helical ramp forms part of a resilient snapping system of the brush stem. It has been found that the holding force of the brush stem decreases rapidly because the snapping system is rapidly worn out after a relatively few insertions. The requirement that the pin of the motor shaft has to be in metal adds significantly to the cost of the oral hygiene device.

OBJECTIVES AND SUMMARY OF THE INVENTION

A principal object of the present invention is to provide an improved automatic insertion system of a stem brush in which the snapping and helical ramp functions are totally separated.

Another object is to provide an insertion system of the foregoing type that utilizes a drive key which possesses minimum wear and tear because the motor shaft may be integrally molded in plastic thereby reducing cost.

A further object is to provide an insertion system of the foregoing type that permits insertion from a multiple of directions.

An important object is to provide an insertion system of the foregoing type with a shorter helical ramp which adds to its strength.

The automatic insertion system of the present invention includes a pair of diametrically opposed driving keys of an integrally molded motor drive shaft. The shaft is also formed with an outwardly projecting annular flange to releasably couple the stem brush to the motor shaft. In this regard, the stem brush includes a pair of slightly flexible longitudinally extending arms provided with internal recesses at their respective free ends that receive the flange of the motor shaft. The stem brush is formed with diametrically opposed slots that receive the driving keys of the motor shaft. In order to assure proper coupling of the stem brush on the motor shaft, a pair of opposed partial sleeves each having two diverging ramps are adapted to embrace the motor shaft. The ramps serve as cam surfaces on which the shaft keys ride during the stem brush insertion to direct the keys into the slots and the shaft annular flange into the recesses in the stem brush arms. The stem brush will then be releasably and drivably coupled to the motor shaft. To release and uncouple the stem brush from the shaft, it need only be pulled to force the arms to flex or spread radially outwardly to force the shaft flange from the recesses in the arms.

DETAILED DESCRIPTION OF PREFERRED EMBODIMENTS

Figure 1:
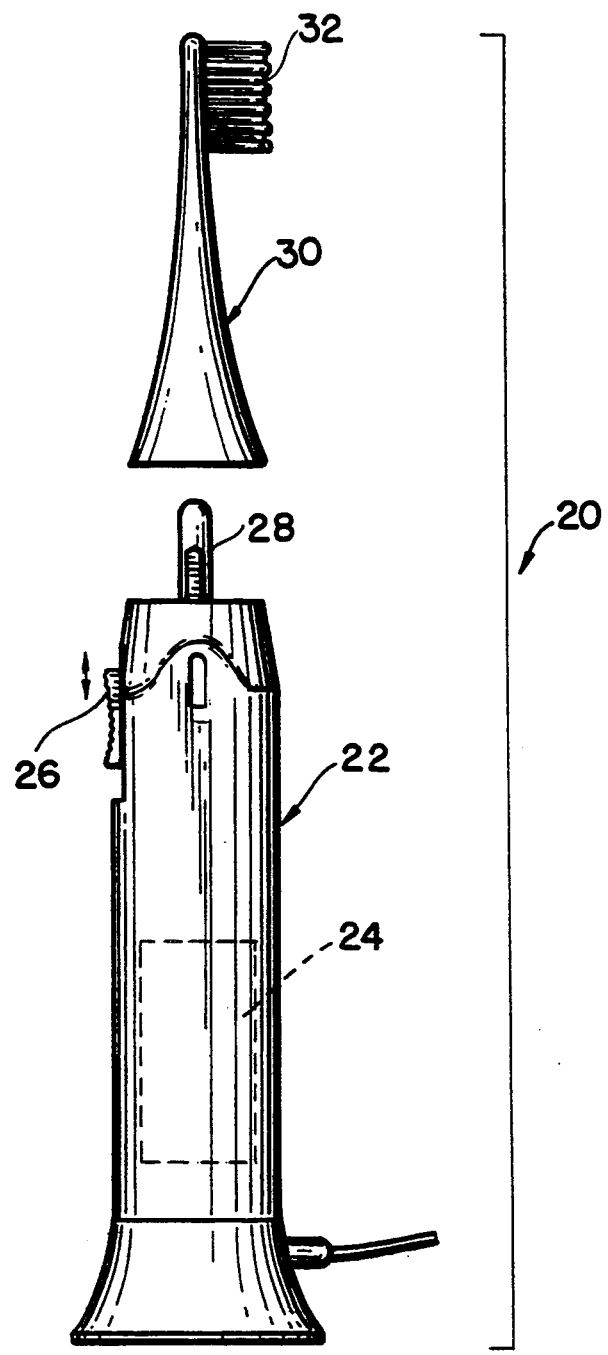
FIG. 1 is an elevational view of a stem brush and handle having incorporated therein the automatic insertion system of the present invention.

The present invention contemplates any type of oral hygiene device, and, particularly, any type of automatic or power driven toothbrush including electrically or battery or rechargeable battery operated devices of this type. Thus, it may comprise electric toothbrush 20 including a handle 22 coupled to a suitable source of electrical energy. A motor 24 (shown in phantom) is activated by switch 26 for varying the output speed of shaft 28, which is adapted to be releasably coupled with stem brush 30 having a tip with bristles of the selected pattern of toothbrush 32, as for example, the diamond head pattern of U.S. Pat. Des. No. 279,838.

Figure 2:
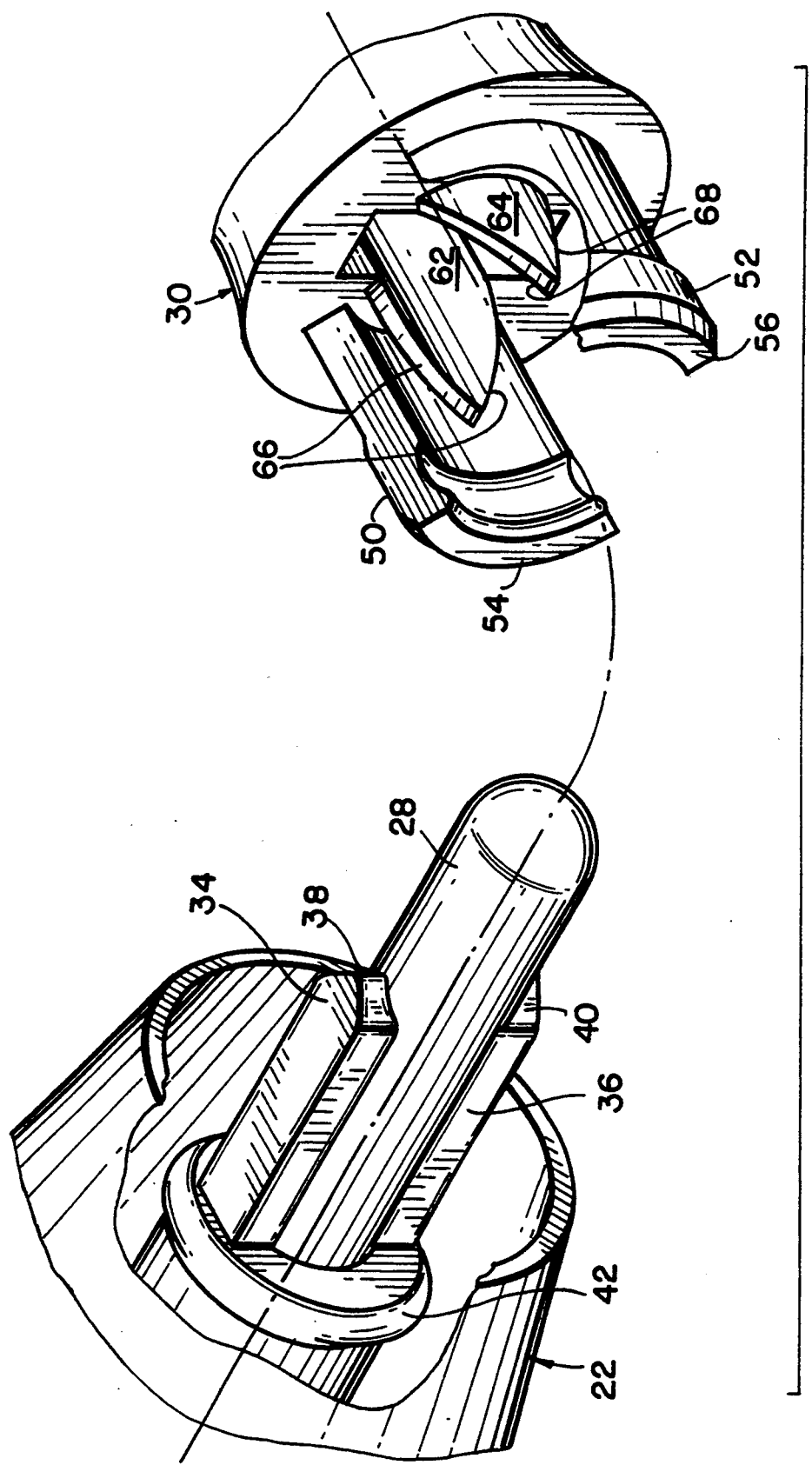
FIG. 2 is an enlarged exploded, and fragmentary perspective view of the base of the stem brush and motor shaft with one of the arms broken away showing the automatic insertion system.
Figure 3:
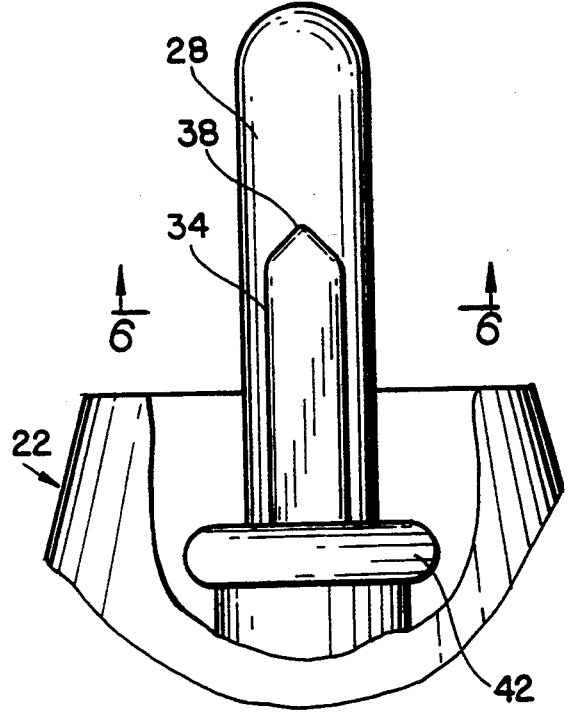
FIG. 3 is an enlarged fragmentary front elevational view of the motor shaft.
Figure 4:
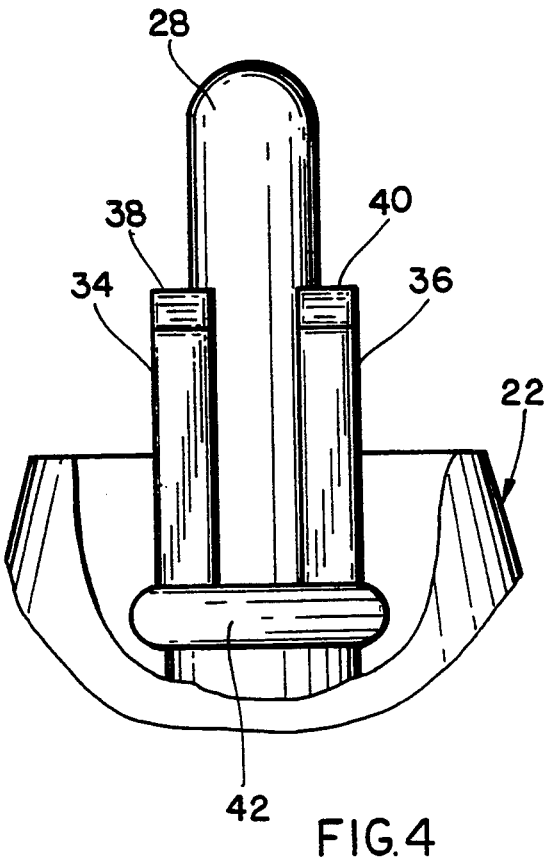
FIG. 4 is a fragmentary side elevational view thereof.
Figure 5:
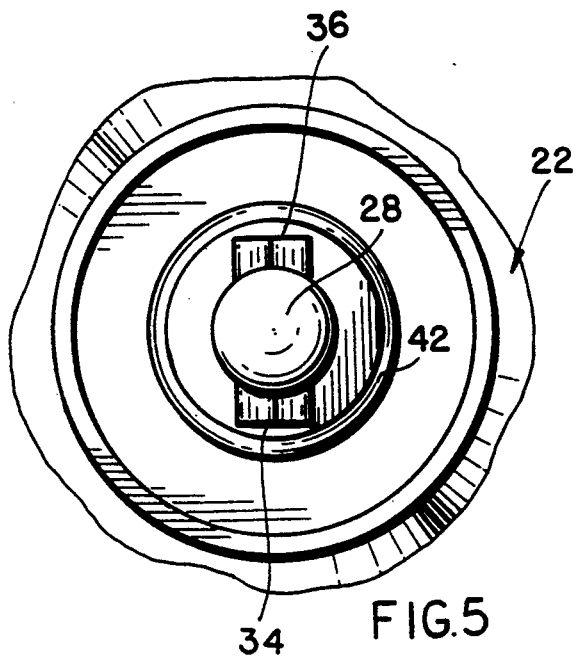
FIG. 5 is a top plan view thereof.
Figure 6:
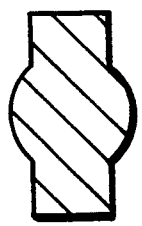
FIG. 6 is a cross sectional view taken along the line 6—6 of FIG. 3.
Figure 7:
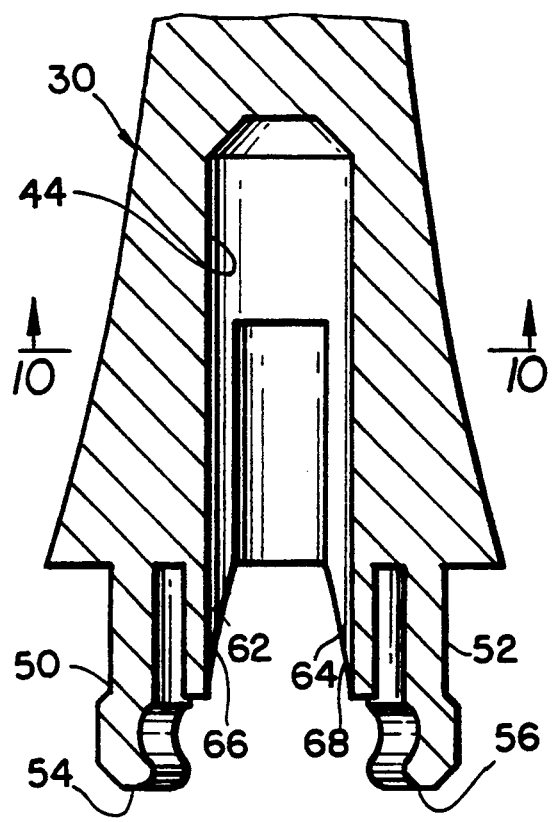
FIG. 7 is a fragmentary longitudinal sectional view of the base of the stem brush.
Figure 8:
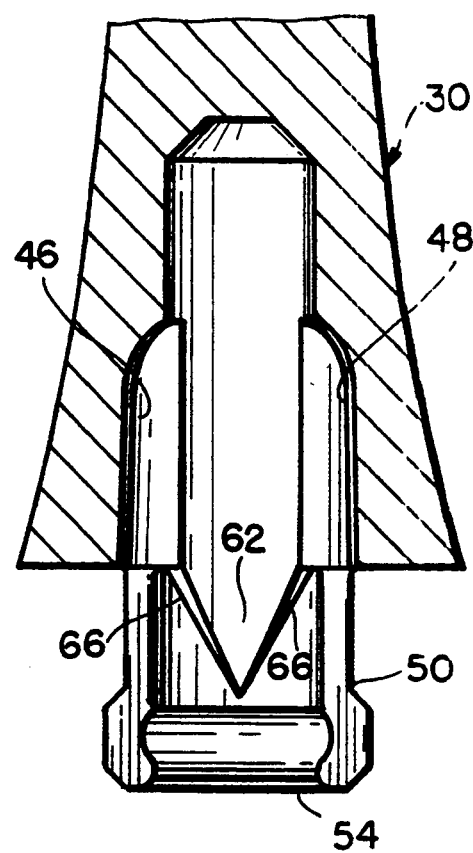
FIG. 8 is another fragmentary longitudinal sectional view taken at 90° to that of FIG. 7.
Figure 9:
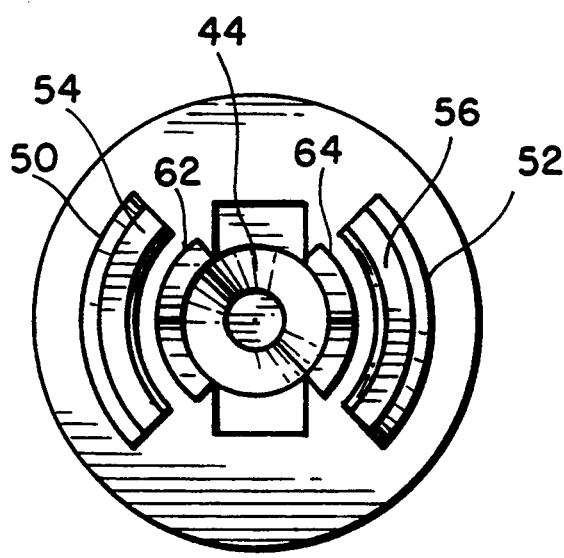
FIG. 9 is a top plan view thereof.
Figure 10:
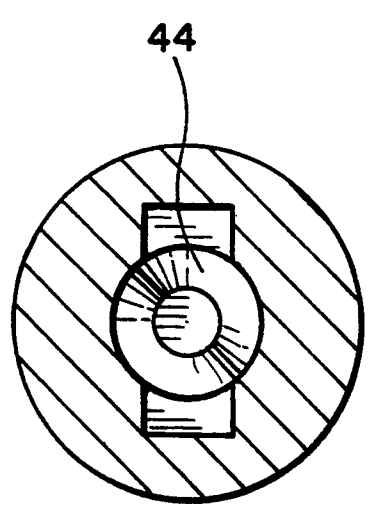
FIG. 10 is a cross sectional view taken along the line 10—10 of FIG. 7.
Figure 11:
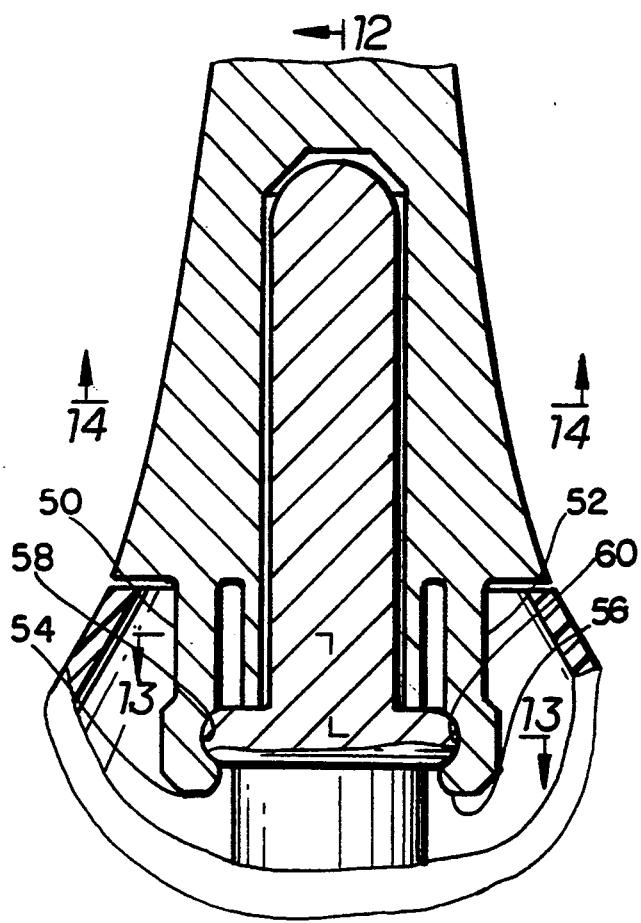
FIG. 11 is a fragmentary longitudinal sectional view of the base of the stem brush coupled to the motor shaft.
Figure 12:
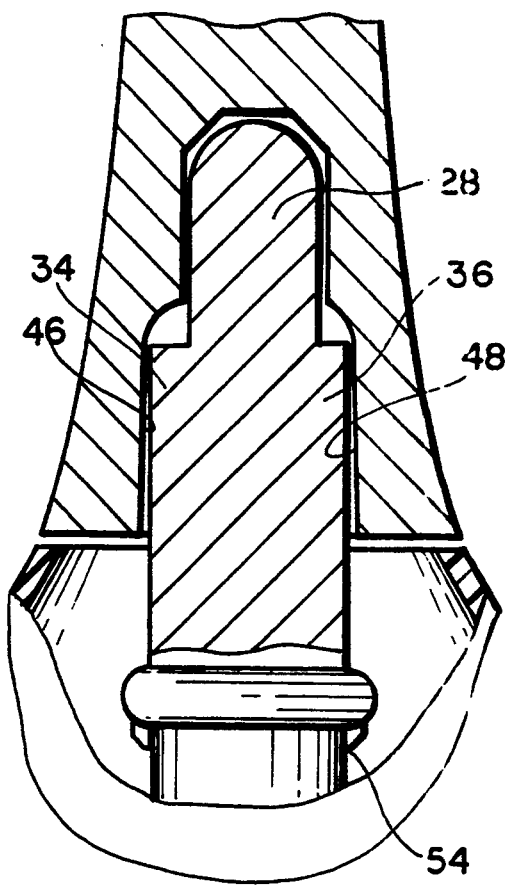
FIG. 12 is another fragmentary longitudinal sectional view at 90° thereto.
Figure 13:
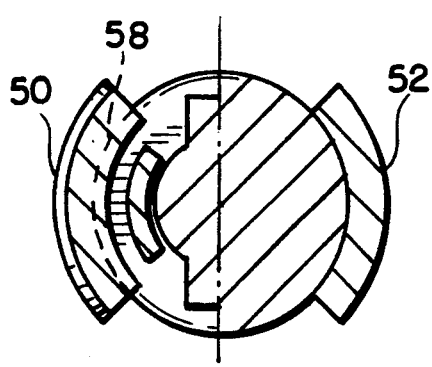
FIG. 13 is a cross sectional view taken along the line 13—13 of FIG. 11.
Figure 14:
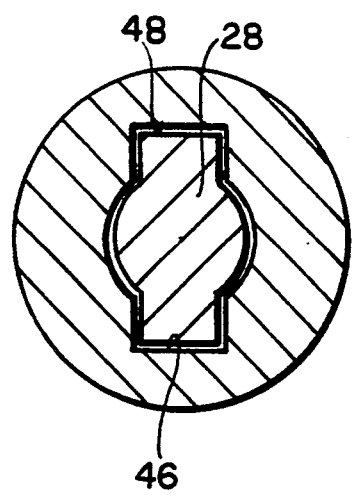
FIG. 14 is a cross sectional view taken along the line 14—14 of FIG. 11.

The automatic insertion system of the present invention for guiding and releasably coupling the base of the stem brush 30 onto the motor shaft 28 is shown in detail in FIGS. 2–14. Referring initially to the motor drive shaft 28, it will be noted that this member is advantageously integrally molded from plastic material thereby enabling this member to be made at reduced costs. A pair of diametrically opposed integral stem brush driving keys 34 and 36 form part of the shaft and have tapered leading ends 38 and 40, respectively. An integral radially outwardly projecting flange 42 at the base of the keys 34 and 36 cooperate in releasably coupling the stem brush 30 to shaft 28.

Referring now to the stem brush 30, its base is formed with bore 44 for receiving the motor drive shaft 28. Diametrically opposed slots 46 and 48 receive the respective keys 34 and 36 to thereby drivably connect the stem brush 30 to the shaft 28. A pair of arms 50 and 52 extend longitudinally from the base of the stem brush and are slightly flexible in a radial direction. The distal ends 54 and 56 of the respective arm 50 and 52 are formed with internal recesses 58 and 60, respectively, for receiving the flange 42 to releasably couple the stem brush 30 to the shaft 28.

A pair of diametrically opposed sleeves 62 and 64 serve to guide the keys 34 and 36 into the respective slots 46 and 48 during the stem brush insertion process. Sleeves 62 and 64 are formed with tapered or helical edges or ramps 66 and 68 that serve as cam faces for engaging the tips 38 and 40 of the respective keys 34 and to guide the keys into slots 46 and 48, respectively. The provision of a pair of tapered sleeves 62 and 64 permits the design of shorter sleeves and ones that are stronger and further permits either of two orientations at the stem brush 30 that are 180° apart. This allows handicapped individuals or those that do not possess manual dexterity to mount the stem brush more easily.

Thus, in operation and when it is desired to mount the stem brush 30 on the handle 22, the individual grasps the handle 22 in one hand and the stem brush 30 in the other. Without necessarily being concerned about orientation, the individual directs the base of the stem brush 30 over the motor shaft 28 so that the shaft enter base 44. The tips 38 and 40 of the respective keys 34 and 36 engage the respective arrow-shaped ramps 66 and 68 of sleeve 62 and 64. A camming action occurs with the ramps serving to guide the keys into accommodating slots 46 and 48, respectively, or depending upon the orientation the keys may enter the slots in a reverse manner. Further insertion of the stem brush will cause the arms 50 and 52 to engage flange 42 causing the arms to flex outwardly enabling the flange to enter recesses 58 and 60 with a snap fit. The stem brush 30 is now firmly mounted in place and the individual need only push button 26 to the desired setting for operation of the electric toothbrush. After brushing, the individual, desiring to remove the stem brush 30 for cleaning, or replacement, need only pull the stem brush 30 axially, or with a longitudinal twisting section to flex the arms 50 and 52 radially outwardly to free the flange 42 from the recesses 58 and 60.

Thus the several aforementioned objects and advantages are most effectively attained. Although a single somewhat preferred embodiment has been disclosed and described in detail herein, it should be understood that the invention is in no sense limited thereby and its scope is to be determined by that of the appended claims.

We claim:

1. An oral hygiene device having an automatic stem insertion system comprising:

a handle and a motor driven shaft, a stem coupled with the shaft, the stem insertion system including at least one key, a base receiving the shaft, at least one slot, each slot receiving a key, at least one sleeve having a ramp for receiving and engaging the key when coupling the stem to the handle and with a camming action of the key on the ramp, guiding the key into the slot, and means for releasably coupling the stem on the handle the coupling means including a radially extending flange and at least one flexible arm having a recess receiving the flange whereby upon coupling the stem to the handle, the flange engaging the arm and flexes the arm outwardly and further movement of the stem onto the handle causes the flange to enter the recess with a snap action, and upon withdrawal of the stem from the handle, the flange causes the arm to flex outwardly to release the flange from the recess.

2. The invention according to claim 1 wherein, a pair of diametrically opposed arms with recesses are adapted to be coupled with the flange.

3. An oral hygiene device having an automatic stem insertion system comprising:

a handle and a motor driven shaft, a stem coupled with the shaft, the stem insertion system including at least one key, a base receiving the shaft, at least one slot, each slot receiving a key, at least one sleeve having a ramp for receiving and engaging the key when coupling the stem to the handle and with a camming action of the key on the ramp, guiding the key into the slot, and means for releasably coupling the stem on the handle a pair of diametrically opposed sleeves with ramps being adapted to receive and engage the key.

4. The invention according to claim 3 wherein a pair of diametrically opposed keys are on the shaft for engagement with the sleeves.

5. The invention according to claim 4 wherein a pair of diametrically opposed slots receive the keys.

6. An oral hygiene device having an automatic stem insertion system comprising:

a handle and an axial motor driven shaft extending longitudinally therefrom and having a free distal end and a proximal end, a stem having a base and being coupled with the shaft and being driven thereby, the stem insertion system including at least one key on the shaft, an axial bore in the base of the stem receiving the free distal end of the shaft, at least one slot in the base of the stem open to the bore, each slot receiving a key, at least one coaxial sleeve extending longitudinally from the base of the stem having a ramp for receiving and engaging the key when coupling the stem to the shaft and with a camming action of the key on the ramp, guiding the key into the slot, means for releasably coupling the stem to the shaft including a radially extending coaxial flange at the proximal end of the shaft having a diameter larger than the shaft and at least one flexible coaxial arm extending longitudinally from the stem base having a distal free end and a proximal end, the arm distal free end having an inner recess receiving the flange whereby upon coupling the stem to the shaft, the flange engages the arm and flexes the arm radially outwardly and further movement of the stem onto the shaft causes the flange to enter the recess with a snap action, and upon withdrawal of the stem from the shaft, the flange causes the arm to flex radially outwardly to release the flange from the recess.

7. The invention in accordance with claim 6 wherein a pair of diametrically opposed coaxial flexible arms extend from the base of the stem and being concentric with the base, each arm having the recess adapted to be coupled with the flange.

8. The invention in accordance with claim 6 wherein a pair of diametrically opposed coaxial sleeves with ramps extend from the base of the stem and are adapted to receive and engage the key.

9. The invention in accordance with claim 8 wherein the ramp of each sleeve is arrow-shaped.

10. The invention in accordance with claim 6 wherein a pair of diametrically opposed keys are on the shaft for engagement with the sleeves.

11. The invention in accordance with claim 10 wherein the shaft, keys and flange are integrally molded from plastic.

12. The invention in accordance with claim 11 wherein the keys have a proximal end and a distal end, the distal end having a contoured camming edge for engaging the ramp of the sleeve.

13. The invention in accordance with claim 10 wherein the base of the stem includes a pair of diametrically opposed slots open to the bore for receiving the keys.

14. A stem for an oral hygiene device forming part of an automatic system insertion system comprising:

a stem base adapted to be coupled with a keyed drive shaft of the device, an axial bore in the base of the stem for receiving the shaft, a slot in the base of the stem open to the bore for receiving a key of the shaft, at least one coaxial sleeve extending longitudinally from the base of the stem having a ramp for receiving and engaging the key when coupling the stem to the shaft and with a camming action guiding the key into the slot, at least one flexible coaxial arm extending longitudinally from the base stem having a distal free and a proximal end, the arm distal free end having an inner recess for cooperating with surfaces of the shaft to releasably couple the stem to the shaft, the arm adapted to flex radially outwardly to engage the shaft surfaces with a snap action, and upon withdrawal of the stem from the shaft, the arm is adapted to flex radially outwardly to release the stem from the shaft.

15. The invention in accordance with claim 14 wherein a pair of diametrically opposed coaxial arms extend from the base of the stem and are concentric with the bore, each arm having the inner recess therein.

16. The invention in accordance with claim 15 wherein a pair of diametrically opposed coaxial sleeves with ramps extend from the base of the stem for receiving and engaging the key.

17. The invention in accordance with claim 16 wherein the ramp of each sleeve is arrow-shaped.

18. The invention in accordance with claim 14 wherein the base of the stem includes a diametrically opposed pair of slots open to the bore for receiving the key.

19. The invention in accordance with claim 14 wherein, a pair of diametrically opposed coaxial arms extend from the base of the stem and are concentric with the bore, each arm having the inner recess therein, a pair of diametrically opposed coaxial sleeves with ramps extend from the base of the stem for receiving and engaging the key, the ramp of each sleeve is arrow-shaped, the base of the stem including a diametrically opposed pair of the slots open to the bore for receiving the key.

* * * * *